United States Patent
Wu et al.

(10) Patent No.: US 11,633,883 B2
(45) Date of Patent: Apr. 25, 2023

(54) FILMING METHOD OF PROBE AND PROBE THEREOF

(71) Applicant: Hefei Chart Medical Instrument Co., Ltd., Hefei (CN)

(72) Inventors: Aijiu Wu, Hefei (CN); Sijing Yang, Hefei (CN); Zhen Han, Hefei (CN); Derun Kong, Hefei (CN)

(73) Assignee: HEFEI CHART MEDICAL INSTRUMENT CO., LTD., Hefei (CN)

(*) Notice: Subject to any disclaimer, the term of this patent is extended or adjusted under 35 U.S.C. 154(b) by 796 days.

(21) Appl. No.: 16/686,100

(22) Filed: Nov. 16, 2019

(65) Prior Publication Data

US 2020/0375472 A1 Dec. 3, 2020

(30) Foreign Application Priority Data

May 29, 2019 (CN) .......................... 201910457273.1

(51) Int. Cl.
*B29C 41/14* (2006.01)
*B29C 41/40* (2006.01)
(Continued)

(52) U.S. Cl.
CPC .............. *B29C 41/14* (2013.01); *B29C 41/40* (2013.01); *B29C 41/42* (2013.01); *A61B 5/02154* (2013.01); *A61B 2562/12* (2013.01); *B29K 2007/00* (2013.01); *B29K 2871/02* (2013.01); *B29L 2031/753* (2013.01)

(58) Field of Classification Search
None
See application file for complete search history.

(56) References Cited

U.S. PATENT DOCUMENTS

2014/0350414 A1 11/2014 McGowan et al.

FOREIGN PATENT DOCUMENTS

| CN | 105433930 A | * | 3/2016 |
| CN | 105662386 A | | 6/2016 |

(Continued)

OTHER PUBLICATIONS

Machine translation of CN-105433930-A. Retrieved from worldwide. espacenet.com on Oct. 4, 2022 (Year: 2022).*

*Primary Examiner* — Etsub D Berhanu
*Assistant Examiner* — Samuel C Kim
(74) *Attorney, Agent, or Firm* — Zhigang Ma

(57) ABSTRACT

A filming method of probe and the probe made by the filming method, the method includes following steps: spraying hydrophilic matrix material on the rigid member; injecting liquid polyethylene glycol into an interior, letting the polyethylene glycol coagulate; cutting out the solid polyethylene glycol, letting the cutting surface and the perimeter of the rigid member to be formed in a smooth plane; letting the wedge end of the rigid member insert a liquid latex vertically for immersion, picking up the rigid member and dripping residue, air drying the adhesive layer of the rigid member; upward setting the wedge end of the rigid member, and letting the latex film be heated, melting the solid polyethylene glycol and letting the polyethylene glycol drain away. The method can minimize the nonlinear deviation, simplify the technological process, improves product quality and manufacturing efficiency.

14 Claims, 3 Drawing Sheets

(51) Int. Cl.
 *B29C 41/42* (2006.01)
 *B29K 7/00* (2006.01)
 *B29L 31/00* (2006.01)
 *A61B 5/0215* (2006.01)

(56) References Cited

FOREIGN PATENT DOCUMENTS

GB           2234344  A  *  1/1991   ......... A61B 5/02154
WO    WO-2015156966 A1 * 10/2015   ......... A61B 5/14532

* cited by examiner

FILMING METHOD OF PROBE AND PROBE THEREOF

The present invention relates to technical field of medical devices, and more particularly to a filming method of probe and the probe made by the filming method.

BACKGROUND OF THE INVENTION

Venous manometer is a non-invasive medical device for detecting esophageal venous blood pressure. It is mainly used in the diagnosis, treatment and monitoring of portal hypertension complications which caused by cirrhosis. The probe is a needle shaped shell with a wedge-shaped head and its diameter is less than 2 mm. The shell is composed of a rigid member and a latex film which attached to its surface.

However, the manufacturing process of existing probe is that the injection molded latex film is directly sheathed on the wedge-shaped rigid member. Because the inner diameter of the film sleeve is generally smaller than the outer diameter of the rigid member, and there is a deviation between the wedge film sleeve and the wedge surface sleeve of the rigid member, it is easy to cause the uneven stress around the detection surface or the tension of the film, resulting in the irregular elastic tension of the detection film and in the non-linear deviation of the detection result. In addition, in order to prevent the film sleeve slipping off from the rigid member, it is usually necessary to use adhesive to bond the part where the film sleeve is combined with the rigid member. After the adhesive solidifies, it is easy to cause a local hardening of the latex film, and affect the detection sensitivity of the probe.

SUMMARY OF THE INVENTION

Therefore, the object of the present invention is to provide a filming method of probe, which obtains a probe that has low nonlinear deviation.

The another object of the present invention provides a probe made by the filming method, which applies filming method of probe to obtain a low nonlinear deviation.

The present invention provides a filming method of probe, the probe comprises a rigid member, two ends of the rigid member are permeable, and a mounting hole is made in one end of the rigid member, the other end of the rigid member is wedge-shaped; the method is for film-forming on the probe, and the method includes following steps: (1) spraying at least one hydrophilic matrix material on the outer wall of rigid member; (2) injecting hot molten liquid polyethylene glycol into the inner of the rigid member to condense the polyethylene glycol until the polyethylene glycol is filled and overflows the notch of the wedge surface of the rigid member; (3) cutting out the solid polyethylene glycol which projects out of the wedge surface after the polyethylene glycol is cooled, and letting the cutting surface and the perimeter of the rigid member to be formed in a smooth plane; (4) inserting the wedge end of the rigid member into a liquid latex vertically for immersion first, picking up the rigid member and dripping residue on the rigid member second, air drying the adhesive layer of the rigid member to let the liquid latex which is covered on the surface of on the rigid member to be a latex film third; and (5) upward setting the wedge end of the rigid member, then heating the latex film to vulcanize for obtaining a detecting film, melting the solid polyethylene glycol and letting the polyethylene glycol drain away at the same time.

In the filming method of the present invention, the hydrophilic matrix is one of anionic surfactants, cationic surfactants and nonionic surfactants.

In the filming method of the present invention, step (1) includes following steps: atomizing the hydrophilic matrix first; and static spraying atomized hydrophilic matrix on the rigid member second.

In the filming method of the present invention, step (2) includes following steps: plugging the mounting hole first; upward setting the wedge surface second; and injecting the hot molten liquid polyethylene glycol into the inner through the cut of the wedge surface third.

In the filming method of the present invention, step (3) further includes following steps: collecting the solid polyethylene glycol; melting the solid polyethylene glycol; and returning melted solid polyethylene to step (2) for collecting again.

In the filming method of the present invention, measuring the mass of the probe both before step (2) and after step (3), then computing the mass difference of the two measurements.

In the filming method of the present invention, the mass of the hot molten liquid polyethylene glycol is equal to the mass difference.

In the filming method of the present invention, the liquid latex is natural rubber latex.

In the filming method of the present invention, the equipment of heating the latex film in step (5) is oven, and heating temperature is 110 degrees Celsius.

In the filming method of the present invention, the probe further includes a fluid medium and a sealing valve, the method further includes following steps: (6) injecting the fluid medium into the inner through the mounting hole first, and mounting the sealing valve in the mounting hole second.

In the filming method of the present invention, the probe further includes an optical fiber lead and a fiber optic pressure sensor; the fiber optic pressure sensor is mounted in the inner and fixed in the sealing valve; one end of the optical fiber lead is electrical connected to the fiber optic pressure sensor, the other end of the optical fiber lead is out of the mounting hole.

In the filming method of the present invention, using water cutter for cutting out the solid polyethylene glycol in step (3).

In the filming method of the present invention, step (5) further includes following steps: vulcanizing the latex film for implement modification reaction; and letting the latex film turn to an elastic film.

The present invention also provides a probe, which comprises a rigid member, two ends of the rigid member are permeable, and a mounting hole is made in one end of the rigid member, the other end of the rigid member is wedge-shaped; a detecting film is film-forming on the probe by the filming method.

In the probe of the present invention, the probe further includes a fluid medium and a sealing valve, the fluid medium is accommodated in the inner of the rigid member, the sealing valve is mounted in the mounting hole.

In the probe of the present invention, the probe further includes an optical fiber lead and a fiber optic pressure sensor; the fiber optic pressure sensor is mounted in the inner and fixed in sealing valve; one end of the optical fiber lead is electrical connected to the fiber optic pressure sensor, the other end of the optical fiber lead is out of the mounting hole.

In the probe of the present invention, the rigid member is made of nickel chromium alloy ultra-thin pipe.

In the probe of the present invention, the probe is used for detecting human blood pressure.

The present invention also provides a manufacturing method of probe, for manufacturing the probe, the manufacturing method includes following steps: providing a rigid member, two ends of the rigid member are permeable, and a mounting hole is made in one end of the rigid member, the other end of the rigid member is wedge-shaped; spraying at least one hydrophilic matrix material on the outer wall of rigid member; injecting hot molten liquid polyethylene glycol into the inner of the rigid member to condense the polyethylene glycol until the polyethylene glycol is filled and overflows the notch of the wedge surface of the rigid member; cutting out the solid polyethylene glycol which projects out of the wedge surface after the polyethylene glycol is cooled, and letting the cutting surface and the perimeter of the rigid member to be formed in a smooth plane; inserting the wedge end of the rigid member into a liquid latex vertically for immersion first, picking up the rigid member and dripping residue on the rigid member second, air drying the adhesive layer of the rigid member to let the liquid latex which is covered on the surface of on the rigid member to be a latex film third; upward setting the wedge end of the rigid member, then heating the latex film to vulcanize for obtaining a detecting film, melting the solid polyethylene glycol and letting the polyethylene glycol drain away at the same time; cleaning the surface and the inner of the rigid member; and injecting a fluid medium into the inner through the mounting hole first, mounting a sealing valve in the mounting hole second.

In the manufacturing method of the present invention, which further mounting a fiber optic pressure sensor into the inner of the rigid member, and fixing the fiber optic pressure sensor in the sealing valve; and electrical connecting one end of an optical fiber lead to the fiber optic pressure sensor, then letting the other end of the optical fiber lead out of the mounting hole.

Solution of the present invention, for solving the above problem, is that apply the above filming method of probe for manufacturing a probe which with a low nonlinear deviation. The filming method sprays hydrophilic matrix material on the rigid member first, injects liquid polyethylene glycol into the inner second, cuts out solid polyethylene glycol third, forms a latex film fourth, lets the latex film be heated to vulcanize and melts the solid polyethylene glycol fifth, thus, a detecting probe is formed on the wedge surface. The hydrophilic matrix material on the rigid member can enhance the compactness and adhesion between the latex film and the rigid member, it not only saves binder and other auxiliary materials, but also improves the sealing performance of the probe. In the present invention, as a result of the detecting film has no form-position error, so the surface of the detecting film is in a state of natural flattening, isotropic stress has more balanced expansion. Therefore, the method can minimize the nonlinear deviation, it not only can simplify the technological process of membrane sleeve processing and package production, but also improves product quality and manufacturing efficiency.

BRIEF DESCRIPTION OF THE DRAWINGS

The above objects and advantages of the present invention will become more readily apparent to those ordinarily skilled in the art after reviewing the following detailed description and accompanying drawings, in which.

DETAILED DESCRIPTION OF PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

First Embodiment

Figure 1:
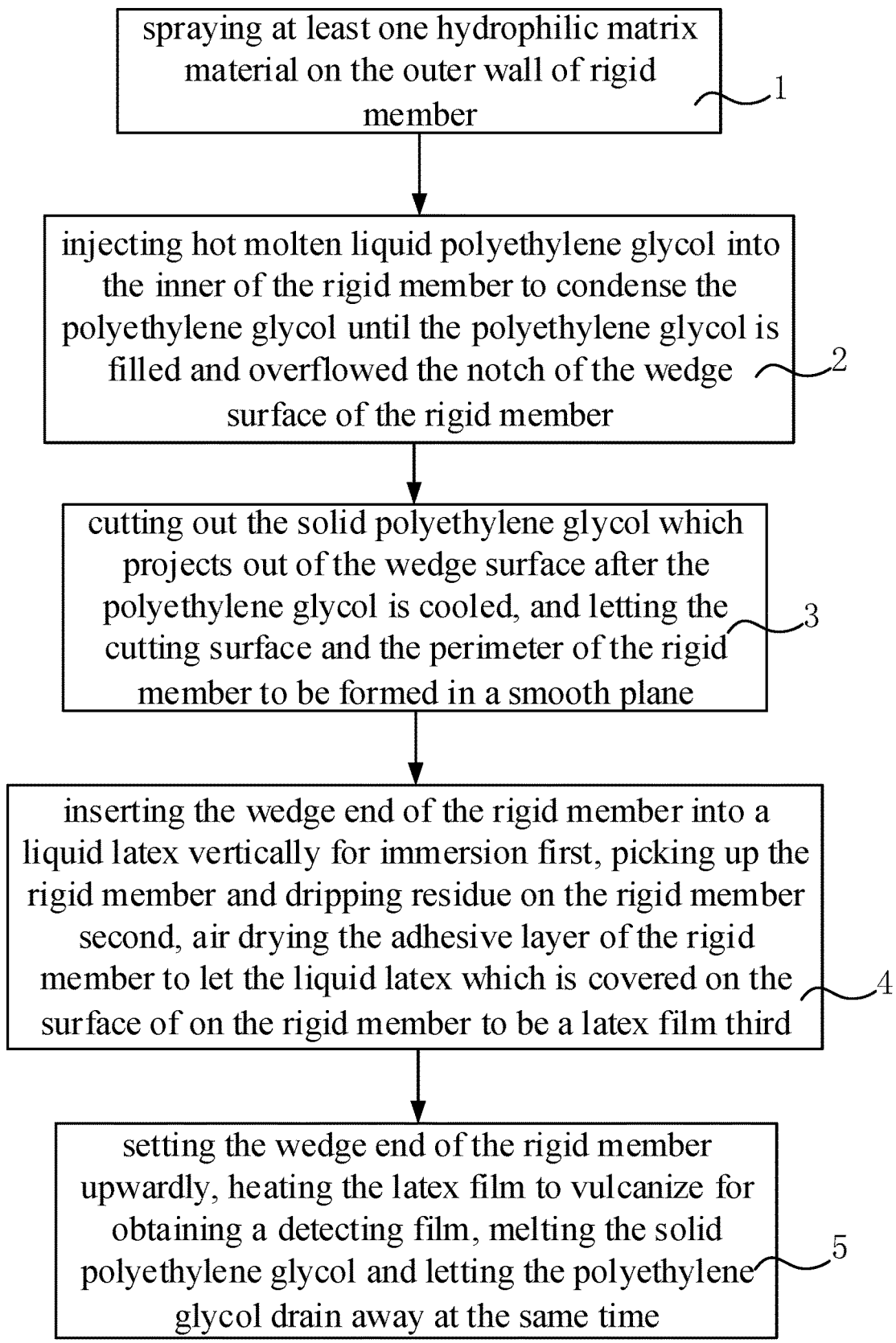
FIG. 1 is a flow chart of the filming method of probe, according to the first embodiment.
Figure 2:
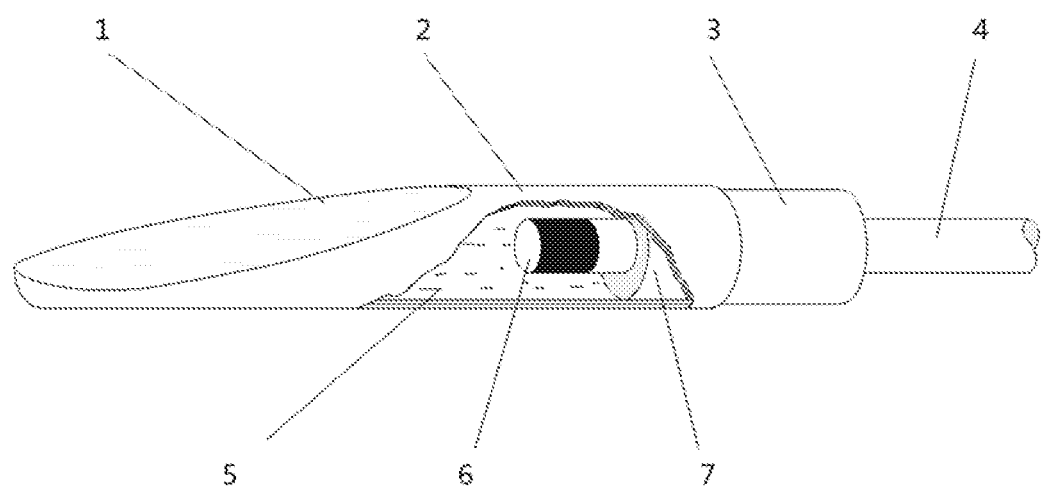
FIG. 2 is a diagram of the structure of the probe which provided in the first embodiment and the other embodiment.

Referring to FIGS. 1 and 2, a filming method of probe is shown as an embodiment. The probe includes a rigid member 3, two ends of the rigid member 3 are permeable, and a mounting hole is made in one end of the rigid member 3, the other end of the rigid member 3 is wedge-shaped. The method is for film-forming on the probe. The rigid member 3 may be made by nichrome tubing, the axial side of the front end is prefabricated into a wedge plane, and the mounting hole at the back end can be inserted for other devices to install. In this embodiment, the filming method includes following steps (from step (1) to step (5)).

Step (1): spraying at least one hydrophilic matrix material on the outer wall of the rigid member 3. The hydrophilic matrix is one of anionic surfactants, cationic surfactants and nonionic surfactants, but in other embodiments, the hydrophilic matrix may be other surfactants. This step includes atomizing the hydrophilic matrix first, static spraying atomized hydrophilic matrix on the rigid member 3 second. Namely, after processing, a layer of hydrophilic material is sprayed on the outside of the rigid member 3 which forms a smooth wedge plane, so as to enhance the compactness and adhesion between the plastic film sleeve and the rigid member 3, which not only saves auxiliary materials such as binder, but also improves the sealing performance of the probe shell.

Step (2): injecting hot molten liquid polyethylene glycol into the inner of the rigid member to condense the polyethylene glycol until the polyethylene glycol is filled and overflows the notch of the wedge surface of the rigid member 3. The melting point of the liquid polyethylene glycol is about 65 degrees Celsius. Specifically, this step includes plugging the mounting hole first, upward setting the wedge surface second, and injecting the hot molten liquid polyethylene glycol into the inner through the cut of the wedge surface third.

Step (3): cutting out the solid polyethylene glycol which projects out of the wedge surface after the polyethylene glycol is cooled, and letting the cutting surface and the perimeter of the rigid member 3 to be formed in a smooth plane. Manufacturing personnel may use water cutter for cutting out the solid polyethylene glycol in this step. In this way, this step can facilitate the subsequent film formation on the smooth surface and avoid the damage caused by the collision between the film formed later and the notch on the wedge plane. In addition, the solid polyethylene glycol in the wedge plane can play a supporting role and provide a template for subsequent film formation, thus forming a dense and stable film.

Step (4): inserting the wedge end of the rigid member 3 into a liquid latex vertically for immersion first, picking up the rigid member 3 and dripping residue on the rigid member 3 second, air drying the adhesive layer of the rigid member 3 to let the liquid latex which is covered on the surface of on the rigid member 3 to be a latex film third, so that the liquid latex on the outer wall of the rigid member 3 can solidify and form a uniform emulsion film 2. In this embodiment, the liquid latex is natural rubber latex. When the rigid member 3 is inserted into the liquid latex, part of the liquid latex will be adsorbed on the wedge end, but there will be some residues, so this step needs to wait for a period of time after picking up the rigid member 3, so that these residues will be dripped under the action of gravity. When air drying the liquid latex on the surface of rigid member 3, some special measures can be used to accelerate the air drying of the liquid latex, such as reducing the air humidity, so as to improve the air drying speed of the liquid latex and the film forming efficiency of the film-forming method.

Step (5): upward setting the wedge end of the rigid member 3, then heating the latex film to vulcanize for obtaining a detecting film, melting the solid polyethylene glycol and letting the polyethylene glycol drain away at the same time. In this embodiment, this step may further includes vulcanizing the latex film for implement modification reaction; and letting the latex film turn to an elastic film. In the specific step of this embodiment, the equipment of heating the latex film is oven, and heating temperature is 110 degrees Celsius. In the process of this step, the latex will undergo the modification reaction, and gradually change from plastic material to elastic material. At the same time, the polyethylene glycol filled in the inner cavity of the rigid member 3 will be heated and melted, and will flow out from the rear end of the rigid member 3 automatically. Thus, the probe film 1 is formed on the wedge plane of the rigid member 3, and then the probe manufacturing is completed through the process of device installation and media packaging. Because there is no form and position error in the detection film 1, the film surface is in a natural flat state after forming, and the stress expansion is balanced in all directions, which can reduce the nonlinear deviation to the maximum extent, and can simplify the processing and production process of the film sleeve, improve the production efficiency of the product.

As described above, the filming method of probe sprays hydrophilic matrix material on the rigid member 3 first, injects liquid polyethylene glycol into the inner second, cuts out solid polyethylene glycol third, forms a latex film fourth, lets the latex film be heated to vulcanize and melts the solid polyethylene glycol fifth, thus, a detecting probe is formed on the wedge surface. The hydrophilic matrix material on the rigid member 3 can enhance the compactness and adhesion between the latex film and the rigid member 3, it not only saves binder and other auxiliary materials, but also improves the sealing performance of the probe. In the present invention, as a result of the detecting film has no form-position error, so the surface of the detecting film is in a state of natural flattening, isotropic stress has more balanced expansion. Therefore, the method can minimize the nonlinear deviation, it not only can simplify the technological process of membrane sleeve processing and package production, but also improves product quality and manufacturing efficiency.

Second Embodiment

A filming method of probe is shown as an embodiment, and some contents are added on the basis of the first embodiment. In this embodiment, step (3) further includes collecting the solid polyethylene glycol, melting the solid polyethylene glycol and returning melted solid polyethylene to step (2). Therefore, the removed solid polyethylene glycol will not be directly wasted, but can be reused, which can improve the utilization rate of polyethylene glycol materials, reduce the cost of materials, avoid the direct discharge of solid polyethylene glycol, and realize the effective utilization of resources.

Third Embodiment

A filming method of probe is shown as an embodiment, some contents are added on the basis of the second embodiment. The method further includes measuring the mass of the probe both before step (2) and after step (3), then computing the mass difference of the two measurements. And the mass of the hot molten liquid polyethylene glycol is equal to the mass difference. In this way, the mass of liquid polyethylene glycol needed for each film formation can be measured accurately, and the corresponding amount of liquid polyethylene glycol can be filled accordingly. On the one hand, the method can improve the film-forming efficiency, on the other hand, it can facilitate the mass film-forming and improve the manufacturing efficiency of the probe. In addition, in other embodiments, the injection quality of the liquid polyethylene glycol can also add a coefficient to the mass difference, which can be set according to the actual needs to ensure that the polyethylene glycol is filled and overflows the notch of the wedge plane.

Fourth Embodiment

Figure 3:
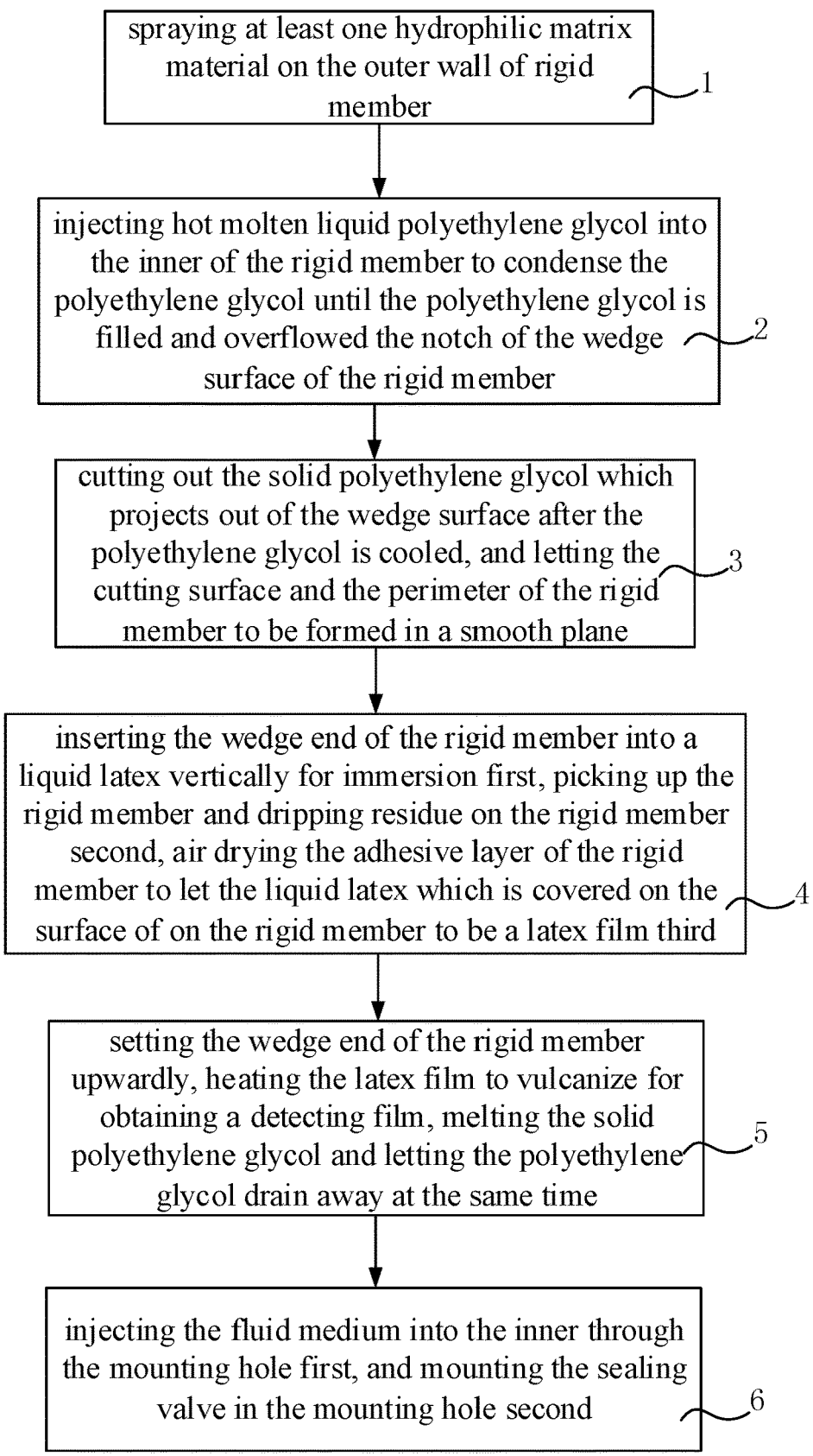
FIG. 3 is a flow chart of the filming method of probe, according to the fourth embodiment.

Referring to FIG. 3, a filming method of probe is shown as an embodiment, some contents are added on the basis of the first embodiment. The probe further includes a fluid medium 5 and a sealing valve 7. The filming method further includes: (6) injecting the fluid medium 5 into the inner through the mounting hole first, and mounting the sealing valve 7 in the mounting hole second. In this way, the filling work of the fluid medium 5 is completed to facilitate the subsequent installation of other components. After adding this step, the method can realize the installation and filling of the probe, and the detection function can be realized because the detection membrane can transmit vibration with the fluid medium 5.

Fifth Embodiment

Referring to FIG. 2 again, a probe is shown as an embodiment. The probe includes a rigid member 3, two ends of the rigid member 3 are permeable, and a mounting hole is made in one end of the rigid member 3, the other end of the rigid member 3 is wedge-shaped. A detecting film is film-forming on the probe by the method which is shown in the first embodiment. Among them, the rigid member 3 is made of nickel chromium alloy ultra-thin pipe, and the probe can be used for detecting human blood pressure.

In order to use the probe better, the probe also includes an optical fiber lead 4, a fluid medium 5, a fiber optic pressure sensor 6, a sealing valve 7, and further includes the probe film 1 and the uniform emulsion film 2 which provided in first embodiment. The fluid medium 5 is accommodated in the inner, the sealing valve 7 is mounted in the mounting hole for sealing fluid medium 5. The fiber optic pressure sensor 6 is mounted in the inner and fixed in sealing valve 7. One end of the optical fiber lead 4 is electrical connected to the fiber optic pressure sensor 6, the other end of the optical fiber lead 4 is out of the mounting hole.

The probe of this embodiment forms the probe film 1 in the hollow area of the wedge plane by shaping a layer of the uniform emulsion film 2 on the wedge plane. In the inner side of the probe film 1, namely, the inner cavity of the rigid member 3 is filled with the fluid medium 5, the fiber optic pressure sensor 6 and the sealing valve 7 are installed, and the optical fiber lead 4 is led out. The external pressure sensed by the probe film 1 is transmitted to the fiber optic pressure sensor 6 through the fluid medium 5, and then the pressure variable is transformed into a grating signal by the fiber optic pressure sensor 6 and transmitted to the interface of the external tester through the optical fiber lead 4. Finally, the grating signal is analyzed and processed by the servo system of the tester to display, report and record the detection data. In the detection process, there is a close mathematical relationship between the deformation of the probe film 1 and the fluid pressure variable. When the probe film 1 adheres to the outer wall of the measured blood vessel, the probe film 1 will undergo stress deformation along with the filling shape of the outer wall of the vessel (outward convex curved surface), That is, the probe film 1 will sink inward. Once the deformation of the interface tends to be static, the blood pressure in the vessel is equal to the fluid pressure in the probe, so as to realize the indirect conduction of the fluid pressure.

Sixth Embodiment

A manufacturing method of probe is shown as an embodiment, and the manufacturing method includes following steps.

(1) Providing a rigid member, two ends of the rigid member 3 are permeable, and a mounting hole is made in one end of the rigid member 3, the other end of the rigid member 3 is wedge-shaped. Manufacturing personnel can pick some rigid blocks for making a rigid member, and setting a mounting hole and a wedge surface in the rigid member 3. In this embodiment, manufacturing personnel select a certain shape and structure of the rigid member 3 according to the actual purpose of the probe and other information.

(2) Spraying at least one hydrophilic matrix material on the outer wall of rigid member 3. This step includes atomizing the hydrophilic matrix first, electrostatic spraying the atomized hydrophilic matrix on the rigid member 3 second. Namely, after processing, a layer of hydrophilic material is sprayed on the outside of the rigid member 3 which forms a smooth wedge plane, so as to enhance the compactness and adhesion between the plastic film sleeve and the rigid member 3, which not only saves auxiliary materials such as binder, but also improves the sealing performance of the probe shell.

(3) Injecting hot molten liquid polyethylene glycol into the inner of the rigid member 3 to condense the polyethylene glycol until the polyethylene glycol is filled and overflows the notch of the wedge surface of the rigid member 3. The melting point of the liquid polyethylene glycol is about 65 degrees Celsius. Specifically, this step includes plugging the mounting hole first, upward setting the wedge surface second, injecting the hot molten liquid polyethylene glycol into the inner through the cut of the wedge surface third.

(4) Cutting out the solid polyethylene glycol which projects out of the wedge surface after the polyethylene glycol is cooled, and letting the cutting surface and the perimeter of the rigid member to be formed in a smooth plane. Manufacturing personnel may use water cutter for cutting out the solid polyethylene glycol in this step. In this way, this step can facilitate the subsequent film formation on the smooth surface and avoid the damage caused by the collision between the film formed later and the notch on the wedge plane. In addition, the solid polyethylene glycol in the wedge plane can play a supporting role and provide a template for subsequent film formation, thus forming a dense and stable film.

(5) Inserting the wedge end of the rigid member 3 into a liquid latex vertically for immersion first, picking up the rigid member 3 and dripping residue on the rigid member 3 second, air drying the adhesive layer of the rigid member 3 to let the liquid latex which is covered on the surface of on the rigid member 3 to be a latex film third, so that the liquid latex on the outer wall of the rigid member 3 can solidify and form a uniform emulsion film 2. In this embodiment, the liquid latex is natural rubber latex. When the rigid member 3 is inserted into the liquid latex, part of the liquid latex will be adsorbed on the wedge end, but there will be some residues, so this step needs to wait for a period of time after picking up the rigid member 3, so that these residues will be dripped under the action of gravity. When air drying the liquid latex on the surface of rigid member 3, some special measures can be used to accelerate the air drying of the liquid latex, such as reducing the air humidity, so as to improve the air drying speed of the liquid latex and the film forming efficiency of the film-forming method.

(6) Upward setting the wedge end of the rigid member 3, then heating the latex film to vulcanize for obtaining a detecting film, melting the solid polyethylene glycol and letting the polyethylene glycol drain away at the same time. In the specific step of this embodiment, the equipment of heating the latex film is oven, and heating temperature is 110 degrees Celsius. In the process of this step, the latex will undergo modification reaction, and gradually change from plastic material to elastic material. At the same time, the polyethylene glycol filled in the inner cavity of the rigid member 3 will be heated and melted, and will flow out from the rear end of the rigid member 3 automatically. Thus, the probe film 1 is formed on the wedge plane of the rigid member 3, and then the probe manufacturing is completed through the process of device installation and media packaging. Because there is no form and position error in the detection film 1, the film surface is in a natural flat state after forming, and the stress expansion is balanced in all directions, which can reduce the nonlinear deviation to the maximum extent, and can simplify the processing and production process of the film sleeve, improve the production efficiency of the product.

(7) Cleaning the surface and the inner of the rigid member 3. And before Cleaning, manufacturing personnel may install the components connected to the sealing valve 7 on the sealing valve 7.

(8) Mounting a fiber optic pressure sensor 6 into the inner of the rigid member 3, and fixing the fiber optic pressure sensor 6 in a sealing valve 7. After completing this step, the fixed installation of fiber optic pressure sensor 6 is completed.

(9) Electrical connecting one end of an optical fiber lead 4 to the fiber optic pressure sensor 6, then letting the other end of the optical fiber lead 4 out of the mounting hole. After completing this step, the connection between the optical fiber lead 4 and the fiber optic pressure sensor 6 is realized to facilitate the signal transmission between them.

(10) Injecting a fluid medium 5 into the inner through the mounting hole first, mounting the sealing valve 7 in the mounting hole second. In this way, the probe is installed. In this way, the whole probe manufacturing process is over.

As described above, the external pressure sensed by the probe film 1 is transmitted to the fiber optic pressure sensor 6 through the fluid medium 5, and then the pressure variable is transformed into a grating signal by the fiber optic pressure sensor 6 and transmitted to the interface of the external tester through the optical fiber lead 4. Finally, the grating signal is analyzed and processed by the servo system of the tester to display, report and record the detection data. In the detection process, there is a close mathematical relationship between the deformation of the probe film 1 and the fluid pressure variable. When the probe film 1 adheres to the outer wall of the measured blood vessel, the probe film 1 will undergo stress deformation along with the filling shape of the outer wall of the vessel (outward convex curved surface), That is, the probe film 1 will sink inward. Once the deformation of the interface tends to be static, the blood pressure in the vessel is equal to the fluid pressure in the probe, so as to realize the indirect conduction of the fluid pressure.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A filming method of a probe, the probe comprising a rigid member, wherein two ends of the rigid member are permeable, a mounting hole is defined in one of the two ends of the rigid member, and the other of the two ends of the rigid member is a wedge-shaped end; the method comprising:
    (1) spraying at least one hydrophilic matrix material on an outer wall of the rigid member;
    (2) plugging the mounting hole, injecting molten liquid polyethylene glycol into an interior of the rigid member until the interior is filled and the molten liquid polyethylene glycol overflows out of a notch of a wedge surface of the wedge-shaped end of the rigid member;
    (3) cutting out solid polyethylene glycol which projects out of the wedge surface after the molten liquid polyethylene glycol is cooled, wherein the cutting forms a cut surface, wherein the cut surface and the perimeter of the rigid member form a smooth plane;
    (4) inserting the wedge-shaped end of the rigid member into a liquid latex vertically for immersion first, picking up the rigid member and dripping off residue of the rigid member second, and air drying the liquid latex which covers the cut surface of the rigid member to form a latex film third; and
    (5) setting the wedge-shaped end of the rigid member upwardly, heating the latex film to vulcanize the latex film for obtaining a detecting film, unplugging the mounting hole, and simultaneously melting the solid polyethylene glycol and letting the melted polyethylene glycol drain away.

2. The method according to claim 1, wherein the at least one hydrophilic matrix material is one of anionic surfactants, cationic surfactants and nonionic surfactants.

3. The method according to claim 1, wherein step (1) comprises:

atomizing the at least one hydrophilic matrix material; and
electrostatic spraying the at least one atomized hydrophilic matrix material on the outer wall of the rigid member.

4. The method according to claim 1, wherein step (2) comprises:
    plugging the mounting hole;
    setting the wedge surface upwardly; and
    injecting the molten liquid polyethylene glycol into the interior through the notch of the wedge surface.

5. The method according to claim 1, wherein step (3) further comprises:
    collecting the cut-out solid polyethylene glycol; and
    melting the collected solid polyethylene glycol.

6. The method according to claim 1, further comprising measuring a mass of the probe both before step (2) and after step (3), and calculating a mass difference between the two measurements.

7. The method according to claim 1, wherein the liquid latex is natural rubber latex.

8. The method according to claim 1, wherein step (5) uses an oven to heat the latex film at a heating temperature of 110 degrees Celsius.

9. The method according to claim 1, wherein the probe further comprises a fluid medium and a sealing valve; the method further comprising:
    (6) injecting the fluid medium into the interior through the mounting hole first, and mounting the sealing valve in the mounting hole second.

10. The method according to claim 9, wherein the probe further comprises an optical fiber lead and a fiber optic pressure sensor; wherein the fiber optic pressure sensor is mounted in the interior and fixed in the sealing valve; one end of the optical fiber lead is electrically connected to the fiber optic pressure sensor, the other end of the optical fiber lead is out of the mounting hole.

11. The method according to claim 1, further comprising using a water cutter for cutting out the solid polyethylene glycol in step (3).

12. The method according to claim 1, wherein step (5) further comprises:
    letting the latex film turn to an elastic film.

13. A manufacturing method of a probe, the manufacturing method comprising:
    providing a rigid member, wherein two ends of the rigid member are permeable, a mounting hole is made in one of the two ends of the rigid member, and the other of the two ends of the rigid member is a wedge-shaped end;
    spraying at least one hydrophilic matrix material on an outer wall of the rigid member;
    plugging the mounting hole, injecting molten liquid polyethylene glycol into an interior of the rigid member until the interior is filled and the molten liquid polyethylene glycol overflows out of a notch of a wedge surface of the wedge-shaped end of the rigid member;
    cutting out solid polyethylene glycol which projects out of the wedge surface after the molten liquid polyethylene glycol is cooled, wherein the cutting forms a cut surface, wherein the cut surface and the perimeter of the rigid member form a smooth plane;
    inserting the wedge-shaped end of the rigid member into a liquid latex vertically for immersion first, picking up the rigid member and dripping off residue of the rigid member second, and air drying the liquid latex which covers the cut surface of the rigid member to form a latex film third;

upwardly setting the wedge-shaped end of the rigid member, then heating the latex film to vulcanize the latex film for obtaining a detecting film, unplugging the mounting hole, and simultaneously melting the solid polyethylene glycol and letting the melted polyethylene glycol drain away;

cleaning the interior of the rigid member; and injecting a fluid medium into the interior through the mounting hole first, mounting a sealing valve in the mounting hole second.

14. The method according to claim 13, further comprising:

mounting a fiber optic pressure sensor into the interior of the rigid member, and fixing the fiber optic pressure sensor in the sealing valve; and electrically connecting one end of an optical fiber lead to the fiber optic pressure sensor, then letting the other end of the optical fiber lead out of the mounting hole.

\* \* \* \* \*